United States Patent
Lin et al.

(10) Patent No.: US 12,387,841 B2
(45) Date of Patent: Aug. 12, 2025

(54) PORTABLE MEDICAL DEVICE AND MANAGEMENT METHOD THEREOF

(71) Applicant: Industrial Technology Research Institute, Hsinchu (TW)

(72) Inventors: Wei-Chieh Lin, Tainan (TW); Yue-Min Jiang, New Taipei (TW); Min-Yi Hsieh, Taipei (TW); Jian-Ren Chen, Hsinchu (TW); Su-Chen Huang, Taoyuan (TW); Ho-Hsin Lee, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 511 days.

(21) Appl. No.: 17/555,823

(22) Filed: Dec. 20, 2021

(65) Prior Publication Data
US 2023/0197254 A1   Jun. 22, 2023

(51) Int. Cl.
*G16H 40/20* (2018.01)
*G16H 40/40* (2018.01)

(52) U.S. Cl.
CPC ............ *G16H 40/20* (2018.01); *G16H 40/40* (2018.01)

(58) Field of Classification Search
CPC ................................ G16H 40/20; G16H 40/40
USPC ........................................................... 702/57
See application file for complete search history.

(56) References Cited

U.S. PATENT DOCUMENTS

| | | | |
|---|---|---|---|
| 6,771,042 B2 | 8/2004 | Chen | |
| 11,087,878 B2 | 8/2021 | Vesto | |
| 2021/0077712 A1* | 3/2021 | Dave | G16H 40/20 |
| 2021/0221243 A1* | 7/2021 | Kawamoto | B60L 58/16 |
| 2022/0181019 A1* | 6/2022 | Ukrainksy | G16H 40/20 |
| 2024/0006057 A1* | 1/2024 | Edgell | A61F 17/00 |

FOREIGN PATENT DOCUMENTS

| | | |
|---|---|---|
| CN | 109003660 A | 12/2018 |
| CN | 110400424 A | 11/2019 |
| CN | 210248765 U | 4/2020 |
| CN | 112386338 A | 2/2021 |
| TW | I573582 B | 3/2017 |
| TW | I594746 | 8/2017 |
| TW | M546201 | 8/2017 |
| TW | I731833 | 6/2021 |

* cited by examiner

*Primary Examiner* — Lisa M Caputo
*Assistant Examiner* — Joshua L Forristall
(74) *Attorney, Agent, or Firm* — WPAT, PC (57) ABSTRACT

A portable medical device includes a portable medical bag, a plurality of connectors and a processor. These connectors respectively connect the portable medical bag and every medical device contained inside the portable medical bag. The portable medical bag obtains the device management information of each the medical device through these connectors. The device management information includes the remaining power of medical device. The processor calculates the charge strategy information of the corresponding medical device according to the medical device information, address information and device management information. In addition, a management method for portable medical device is also provided.

10 Claims, 6 Drawing Sheets

PORTABLE MEDICAL DEVICE AND MANAGEMENT METHOD THEREOF

TECHNICAL FIELD

The technical field relates to a portable medical device and a management method for the same.

BACKGROUND

In the past, healthcare workers in mobile health care service or home medical care service always need to carry different medical devices and laptop equipment respectively before the visit. An integrated portable medical bag has been introduced to include required medical devices and an inspection record platform. However, some unexpected situations do occur during actual cases. For example, due to the different sizes of accessories for different medical devices, the requirement for setting the accessory flexibly inside the portable medical bag is hardly to meet.

For another example, according to different cases for visiting patient, the usage frequency of individual medical device is different. Therefore, the remaining power capacities of different medical devices are also different. Although the portable medical bag can charge the medical devices, yet the frequently used medical devices may still meet the problem of insufficient power. Since the recharging speed may not meet the actual requirement of healthcare workers, the availability of frequently used medical devices becomes an issue.

In addition, before mobile medical care service or home medical care service be initiated, a healthcare worker needs to check the combination of medical devices according to the requirement for patient visiting. However, during the medical care service, it is inevitable that misses in carrying required medical devices may still occur due to busy work or travel.

Therefore, how to provide a portable medical device and a management method for the same to improve the aforesaid problems will be an urgent issue to the skilled in the art.

SUMMARY

One embodiment of this disclosure provides a portable medical device. The portable medical device includes a portable medical bag, a plurality of connectors and a processor. The portable medical contains a plurality of medical devices. The connectors respectively connected to the medical devices and the portable medical bag. The portable medical bag obtains a device management information, having the remaining power, of each of the medical devices via the corresponding one of the connectors. The processor is disposed in the portable medical bag and receives a medical device information, a positioning information and an address information. The medical device information includes the battery capacity and the charging specification of each of the medical devices, and the processor calculates the charge strategy information of the medical devices according to the medical device information, the address information and the device management information.

Another embodiment of this disclosure provides a management method of portable medical device. The management method includes the following steps: receiving a medical device information, a positioning information and an address information by a processor, wherein the medical device information includes the battery capacity and the charging specification corresponding to each of the medical devices; connecting a plurality of connectors to a portable medical bag and the medical devices respectively; obtaining the device management information from each of the medical devices via the connectors and transmitting the device management information to the portable medical bag, wherein the device management information includes a remaining power; and calculating the charge strategy information of the medical devices by the processor based on the medical device information, the address information and the device management information.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The disclosure will become more fully understood from the detailed description given herein below and the accompanying drawings which are given by way of illustration only, and thus are not limitative of the disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1:
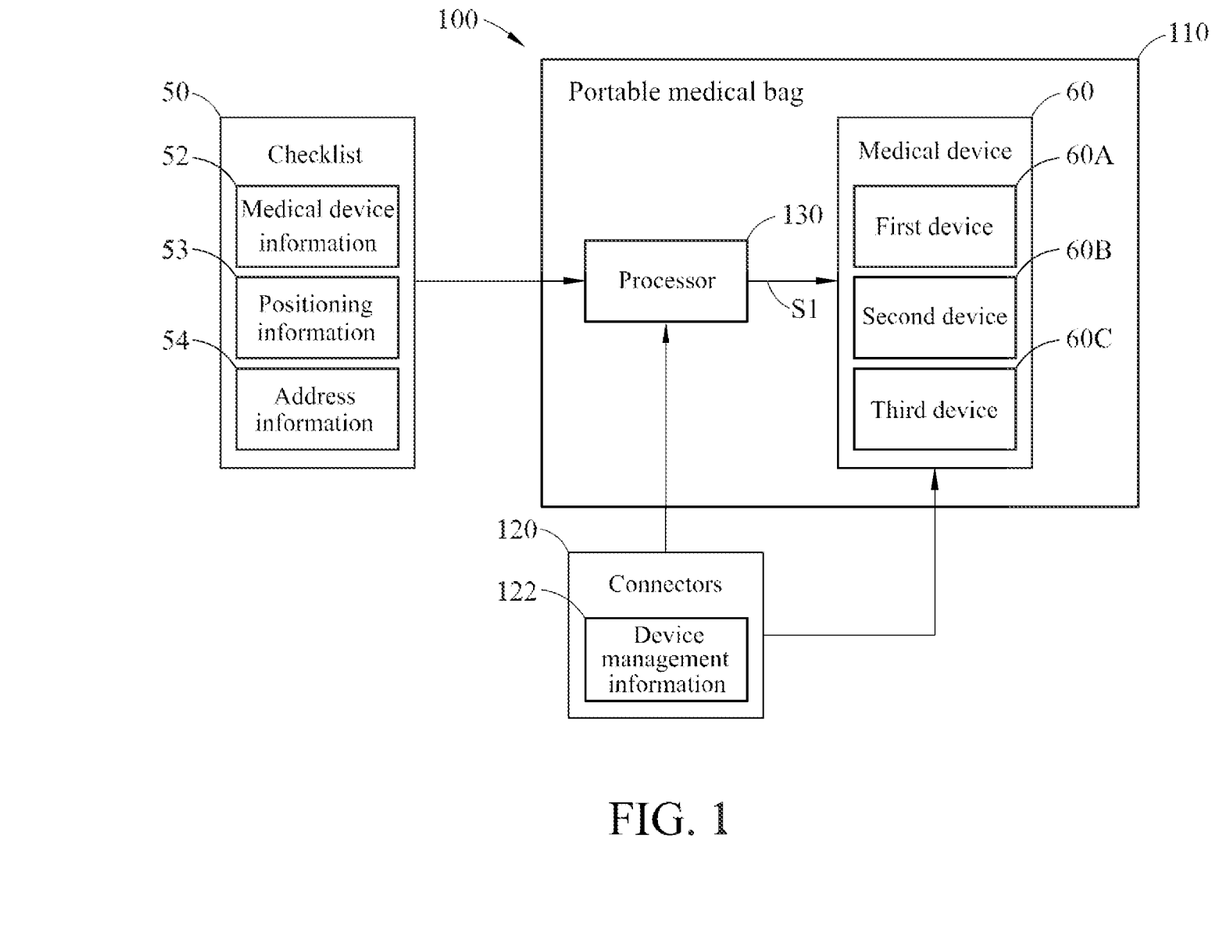
FIG. 1 is a schematic block view of an embodiment of the portable medical device in accordance with this disclosure.

FIG. 1 is a schematic block view of an embodiment of the portable medical device in accordance with this disclosure. As shown in FIG. 1, the portable medical device 100 includes a portable medical bag 110, a plurality of connectors 120 ad a processor 130. The portable medical bag 110 has an internal accommodating space for containing a plurality of medical devices 60. The medical devices 60 may include a first device 60A, a second device 60B and a third device 60C. The types of the first device 60A, the second device 60B and the third device 60C can be changed according to practical inspection requirements. For example, the first device 60A may be a wound treatment device, the second device 60B may be an ultrasonic device, and the third device 60C may be an ophthalmoscope. In this embodiment, the quantity of the medical devices 60 can also be adjusted according to practical inspection requirements.

In this embodiment, the processor 130 is disposed in the portable medical bag 110. The processor 130 receives a medical device information 52, a positioning information 53 and an address information 54 from a checklist 50. The checklist 50 can be obtained by interpreting the physician order issued via the healthcare information system (HIS) of a hospital or a clinic. The checklist 50 includes the information about the items and quantities of the required medical devices 60 for at least one scheduled destination.

Figure 2:
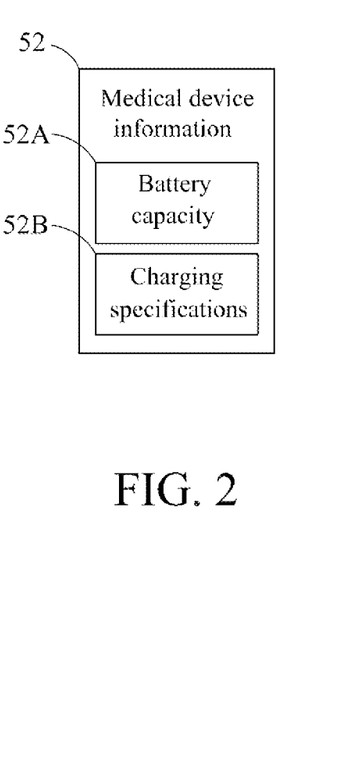
FIG. 2 shows schematically the medical device information in accordance with this disclosure.

In this embodiment, as shown in FIG. 2, the medical device information 52 includes the battery capacity 52A and the charging specification 52B of each of the medical devices 60. The charging specification 52B includes the charge voltage, the charge current and the usage count of the specific medical device 60, and the positioning information 53 includes the positioning coordinates of the destination(s). For instance, the positioning coordinates of each of the destinations may be the GPS coordinates. The address information 54 includes a destination data for providing the expected time for moving to the scheduled destination. The expected time for moving to the scheduled destination can be calculated according to the positioning coordinates of this destination. In other words, the checklist 50 can provide the information about the usage count of any one of the medical devices 60 and the expected time for moving to the scheduled destination.

For example, the checklist 50 shows that the medical devices 60 needed by the destination A include a wound treatment device, an ultrasonic device and an ophthalmoscope. The usage count of the wound treatment device would be 11, that of the ultrasonic device would be 8, and that of the ophthalmoscope would be 2. In addition, the checklist 50 further shows that the 30 minutes is the expected time for a healthcare worker, carrying the portable medical bag 110 containing the above medical devices 60, to move from the hospital or the clinic to the destination A.

Figure 3:
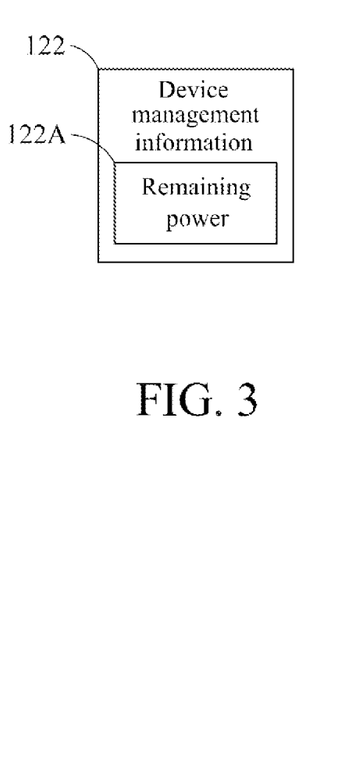
FIG. 3 shows schematically the device management information in accordance with this disclosure.

In this embodiment, the connectors 120 are connected to the portable medical bag 110 and the medical devices 60 respectively. The connectors 120 may be clips or other connecting structures. When the connectors 120 are connected to the medical devices 60, the device management information 122 of the medical devices 120 can be obtained. The device management information 122 includes the remaining power 122A (as shown in FIG. 3) of the medical devices 60. In addition, the device management information 122 also includes the status information of the medical devices 60, such as the battery level, the charge voltage, the charge current, etc., and the device usage records of the medical devices 60, such as the device usage count, the average usage time, etc.

For instance, the healthcare worker can know that the medial devices 60 in the portable medical bag 110 include a wound treatment device, an ultrasonic device and an ophthalmoscope by checking the device management information 122. Besides, the healthcare worker can know the battery level of the wound treatment device is 25%, the charge voltage thereof may be 20, 15, 12, 9 or 5V, the charge current thereof may be 5 or 3 A, the usage count thereof is 24, the average usage time thereof is 30 minutes and the average power consumption thereof is 1.5 Wh by checking the device management information 122. Besides, the healthcare worker can further know that the battery level of the ultrasonic device is 50%, the charge voltage thereof may be 15, 12 or 5V, the charge current thereof may be 5 or 3 A, the usage count thereof is 18, the average usage time thereof is 30 minutes and the average power consumption thereof is 2 Wh by checking the device management information 122. Similarly, the healthcare worker can further know that the battery level of the ophthalmoscope is 70%, the charge voltage thereof may be 15, 12, 9 or 5V, the charge current thereof may be 5 or 3 A, the usage count thereof is 45, the average usage time thereof is 20 minutes and the average power consumption thereof is 1 Wh by checking the device management information 122.

In this embodiment, the connector 120 transmits the device management information 122 received from the medical device 60 to the processor 130 inside the portable medical bag 110. The portable medical bag 110 obtains the device management information 122 of the medial devices 60 (e.g., the first device 60A, the second device 60B and the third device 60C) via the connector 120. The processor 130 calculates a charge strategy information S1 for the medical devices 60 according to the medical device information 52, the address information 54 and the device management information 122. For example, if only 20 minutes are available for charging the medical devices 60 before the healthcare worker arrives the destination A, the charge strategy provided by the charge strategy information S1 needs to appropriately adjust the electrical output so as to charge one or more of the medical devices 60 to the required battery levels by the charge voltage of 12V and the charge current of 3 A within 20 minutes. Taking the destination A as an example, the hourly charged capacity of the wound treatment device is 11.3 Wh, that of the ultrasonic device is 5 Wh, and the ophthalmoscope does not need to be charged. Accordingly, the charge order provided by the charge strategy information S1 for the destination A may be the wound treatment device, the ultrasonic device and the ophthalmoscope. The electrical output for the wound treatment device can be the charge voltage of 12V and the charge current of 3 A. The electrical output for the ultrasonic device can be the charge voltage of 9V and the charge current of 3 A. The electrical output for the ophthalmoscope can be the charge voltage of 5V and the charge current of 3 A.

In this way, according to the device management information 122 and the preloaded checklist 50 transmitted through the connectors 120, the processor 130 can calculate the power supply arrangement, implemented during the time period of the healthcare worker moving from the hospital or clinic to the destination A, for the medical devices 60. The charge order and the charge strategy of the medical devices 60 can be determined according to different output voltages, output currents, charging speeds of the medical devices 60. As a result, the portable medical device 100 can effectively solve the problem of charging discretion under the same charge pattern, and further solve the problem that the charging speeds of some medical devices 60 are insufficient because these medical devices 60 are frequently used. Thus, the portable medical device 100 can achieve a reasonable power management so as to make sure that all medical devices 60 always have enough battery levels when the healthcare worker visits the specific destination.

Figure 4:
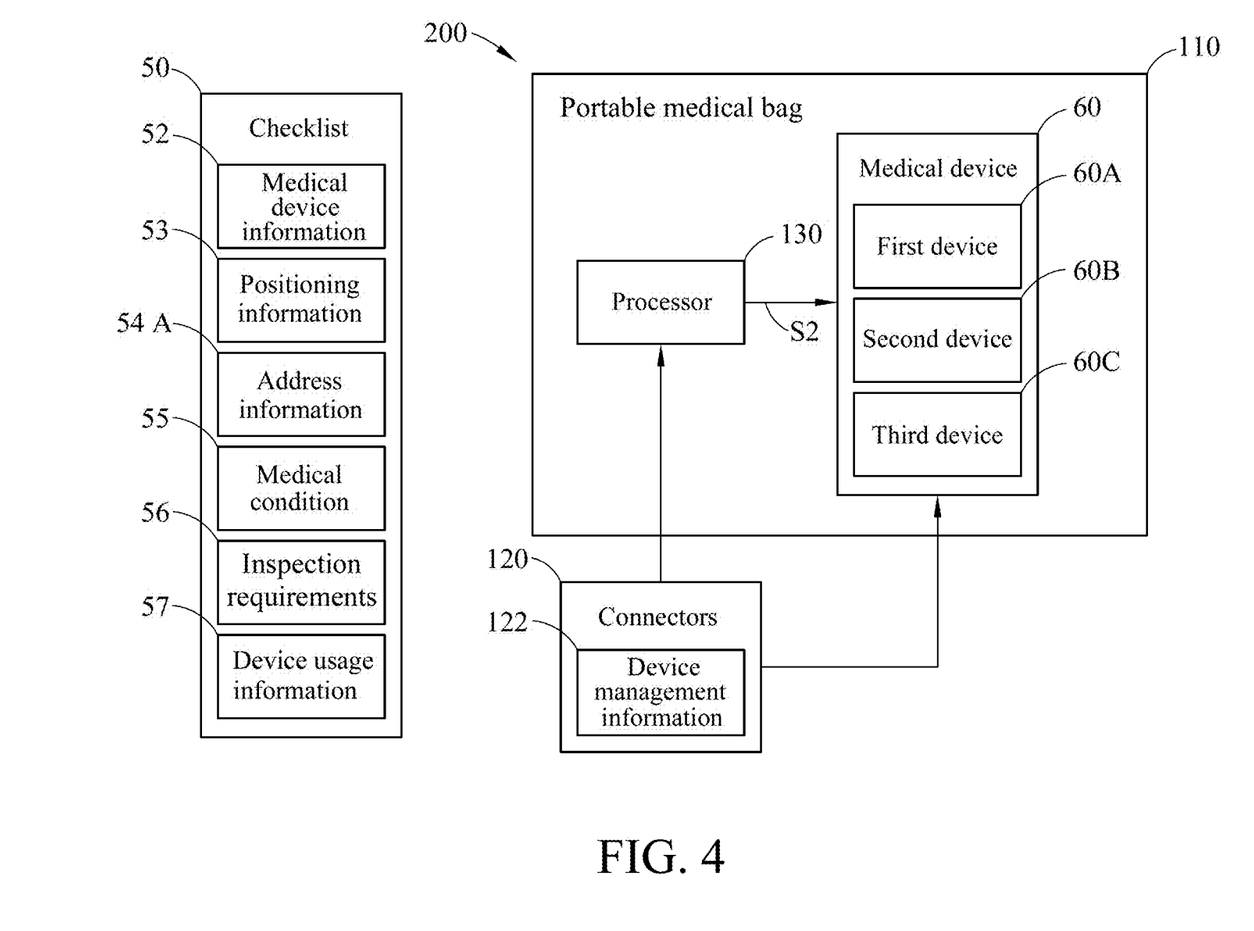
FIG. 4 is a schematic block view of another embodiment of the portable medical device in accordance with this disclosure.

The aforesaid embodiment, describing the case that a healthcare worker moves from a hospital or clinic to a specific destination, is just for illustration instead of limiting the scope of the disclosure. FIG. 4 is a schematic block view of another embodiment of the portable medical device in accordance with this disclosure. As shown in FIG. 4, according to the portable medical device 200 of this embodiment, the checklist 50 further includes a patient condition 55, an inspection requirement 56 and a device usage information 57, and the content of the checklist 50 can be adjusted according to the patient condition 55 and the inspection requirement 56 of the day. There may be several patients to be treated, so there may be also several destinations to be visited. The healthcare worker can know the power consumption of using each of the medical devices 60 for one time according to the device usage information 57. The address information 54A includes the destination data with time sequences, which includes the expected time of the healthcare worker moving from the hospital or clinic to each of the destinations. The expected time of the healthcare worker moving from the hospital or clinic to each of the destinations can be calculated according to the positioning coordinates of each of the destinations.

The processor 130 receives the patient condition 55, the inspection requirement 56 and the device usage information 57. Based on the medical device information 52, the address information 54A including the destination data with the time sequences, the device management information 122, the patient condition 55, the inspection requirement 56 and the device usage information 57, the processor 130 can calculate the charge strategy information S2 and then adjust the destinations with the time sequences in the charge strategy information S2. Therefore, the processor 130 can obtain a task scheduling conforming to the requirements of these destinations.

For instance, the medical devices 60 needed by the healthcare worker visiting the destination A includes a wound treatment device, an ultrasonic device, an ophthalmoscope, and the expected time of the healthcare worker, carrying the portable medical bag 110 having the above medical devices 60, moving from the hospital or clinic to the destination A is 30 minutes. The medical devices 60 needed by the healthcare worker visiting the destination B includes the wound treatment device, the ultrasonic device, the ophthalmoscope, and the expected time of the healthcare worker, carrying the portable medical bag 110 having the above medical devices 60, moving from the destination A to the destination B is 20 minutes. After the processor 130 receives the destination data with the time sequences, the processor 130 estimates that the healthcare worker needs to use one of the medical devices 60 (e.g., the ophthalmoscope) at the destination B and the time for charging this medical device 60 (e.g., the ophthalmoscope) to the required capacity is 25 minutes. However, it is obvious that the expected time (20 minutes) of the healthcare worker moving from the destination A to the destination B is not enough to charge this medical device 60 (e.g., the ophthalmoscope) to the required capacity. As a result, the processor 130 would change this medical device 60 (e.g., the ophthalmoscope) to the required capacity in advance according to the task scheduling before the healthcare worker reaches the destination A.

In one embodiment, as the battery levels of the medical devices 60 may be influenced by some unexpected incidents when the healthcare worker uses the medical devices 60 at each of the destinations, the battery levels of the medical devices 60 may have some deviations. Therefore, if the healthcare worker needs to visit several destinations, the processor would re-calculate the destination data with the time sequences after the work of each of the destinations has been done so as to make sure that the requirements of all of the destinations can be satisfied. In this way, it is ensured that each of medical devices 60 always has enough battery level when the healthcare worker visits each of the destination.

Figure 5:
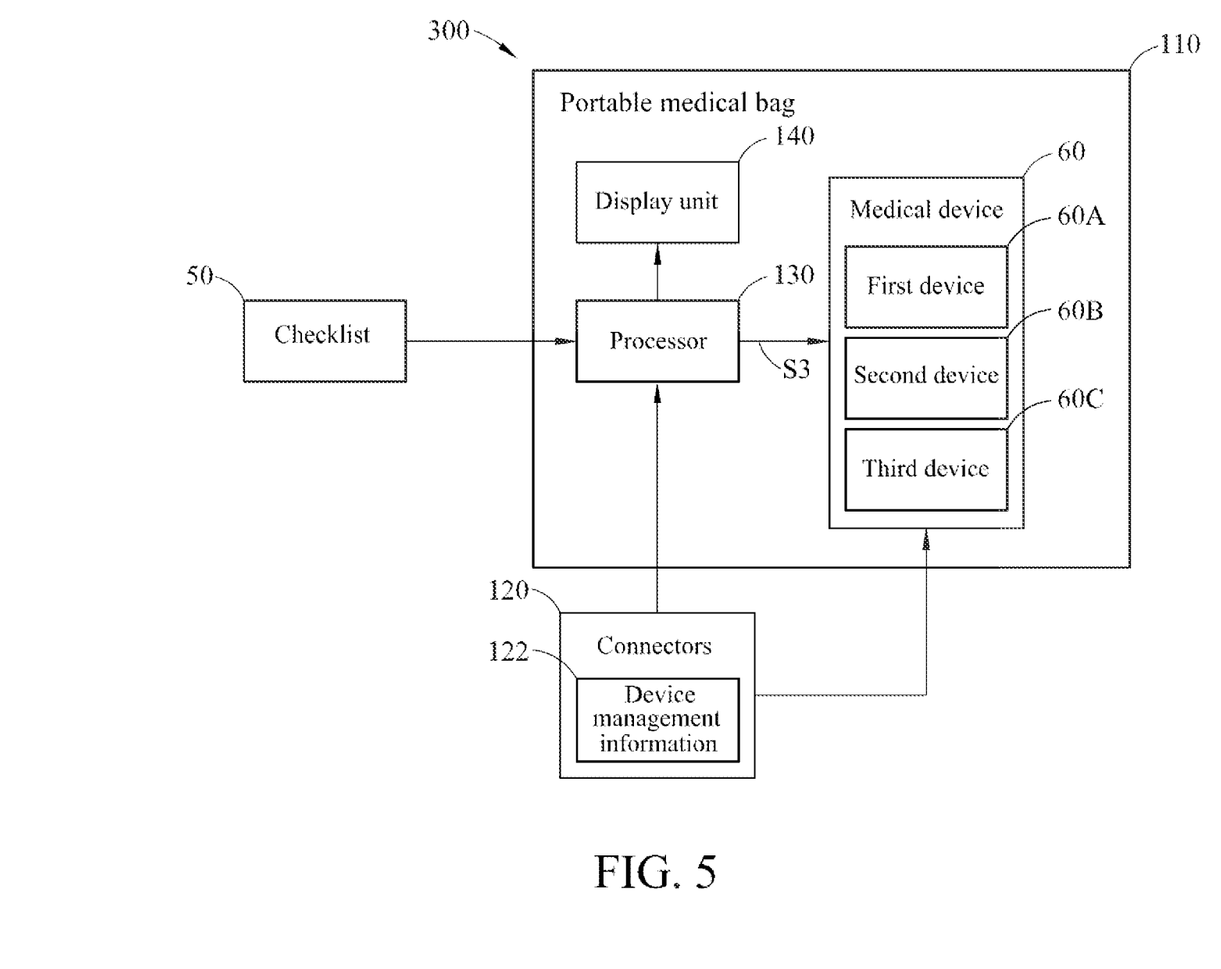
FIG. 5 is a schematic block view of a further embodiment of the portable medical device in accordance with this disclosure.
Figure 6:
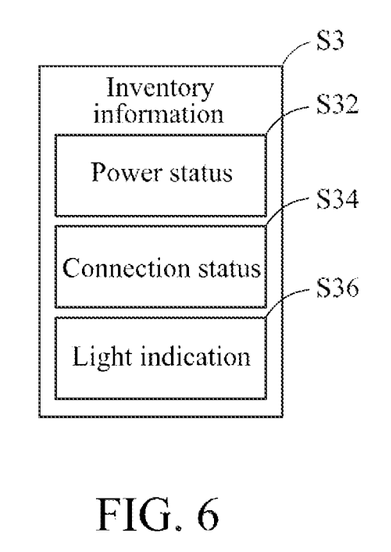
FIG. 6 shows schematically the inventory information in accordance with this disclosure.

FIG. 5 is a schematic block view of a further embodiment of the portable medical device in accordance with this disclosure. According to the portable medical device 300 shown in FIG. 5, when the connectors 120 are connected to the medical devices 60, the device management information 122 of the medical devices 60 can be obtained and transmitted to the processor 130 inside the portable medical bag 110. Then, the processor 130 outputs an inventory information S3 according to the medical device information 52 and the device management information 122. As shown in FIG. 6, the inventory information S3 includes the power status S32, the connection status S34 and the light indication S36 of each of the medical devices 60. In this way, the healthcare worker can take inventory for the medical devices 60 and check the records, including the aforementioned power status S32, connection status S34 and light indication S36, of the medical devices 60 inside the portable medical bag 110.

In one embodiment, the portable medical device 300 further includes a display unit 140. The display unit 140 is disposed inside the portable medical bag 110 and the inventory information S3 can be shown by the display unit 140. Therefore, the display unit 140 can further enhance the convenience of the healthcare worker taking inventory for the medical devices 60 before or after the medical visiting.

Figure 7:
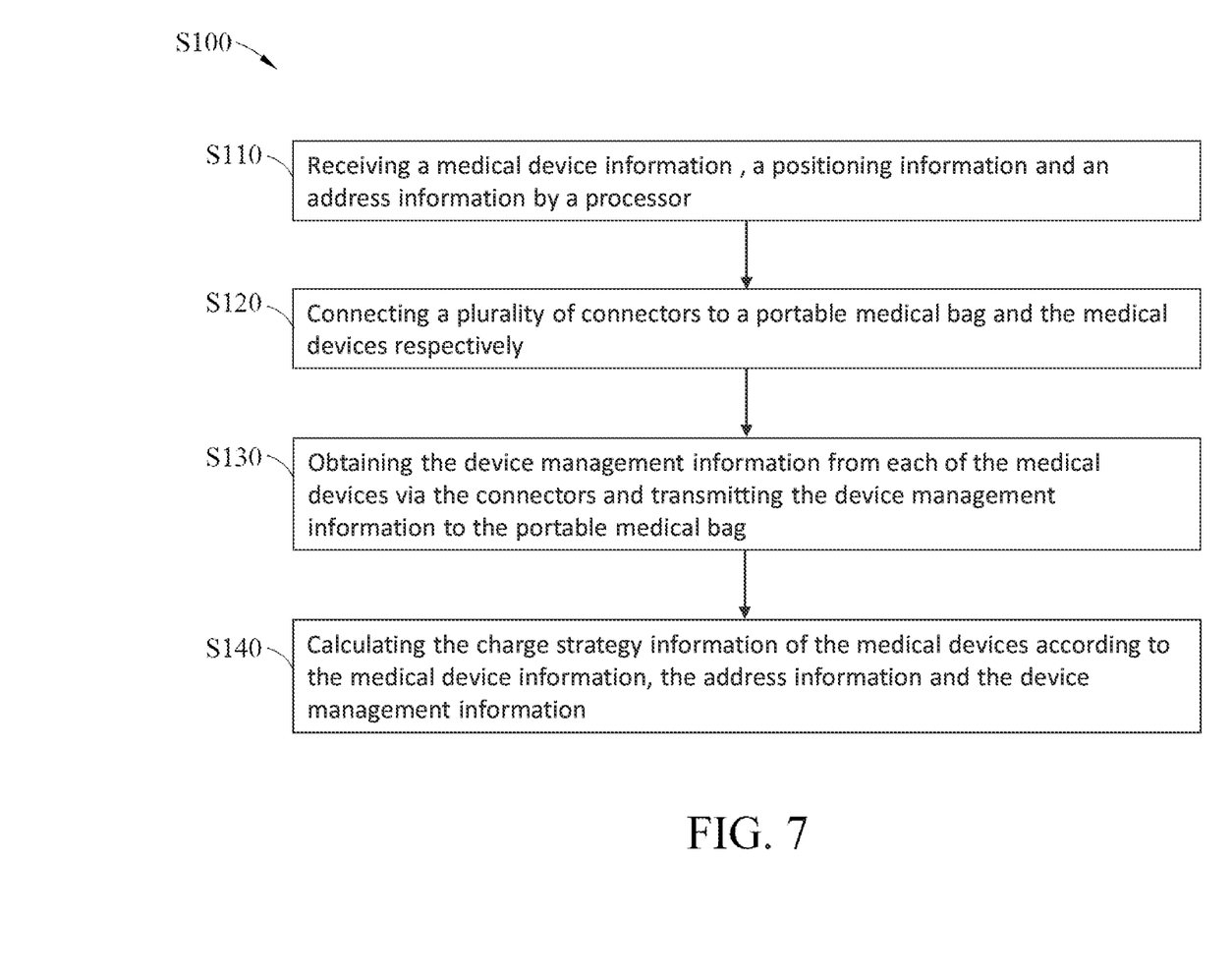
FIG. 7 is a schematic flowchart of an embodiment of the management method of portable medical device in accordance with this disclosure.

FIG. 7 is a schematic flowchart of an embodiment of the management method of portable medical device in accordance with this disclosure. As shown in FIG. 7, in this embodiment, the management method of portable medical device S100 includes Step S110 to Step S140 as follows. As shown in FIG. 1, the portable medical bag 110 is used to contain a plurality of medical devices 60. The first step is Step S110: receiving a medical device information 52, a positioning information 53 and an address information 54 by a processor 130, wherein the medical device information 52 includes the battery capacity 52A and the charging specification 52B corresponding to each of the medical devices 60. The second step is Step S120: connecting a plurality of connectors 120 to a portable medical bag 110 and the medical devices 60 respectively. Then, the third step is Step S130: obtaining the device management information 122 from each of the medical devices 60 via the connectors 120 and transmitting the device management information 122 to the portable medical bag 110, wherein the device management information 122 includes a remaining power 122A. The final step is Step S140: calculating the charge strategy information S1 of the medical devices 60 according to the medical device information 52, the address information 54 and the device management information 122.

In another embodiment of the disclosure, the following step may be inserted between Step S130~Step S140 or be performed after Step S130~Step S140: outputting an inventory information S3 (as shown in FIG. 5) according to the medical device information 52 and the device management information 122 by the processor 120, wherein the inventory information S3 includes the power status S32, the connection status S34 and the light indication S36 of each of the medical devices 60. Moreover, the inventory information S3 is displayed by the display unit 140.

In another embodiment of the disclosure, the following step may be inserted between Step S130~Step S140 or be performed after Step S130~Step S140: receiving destination data with time sequences by the processor 120 corresponding to a plurality of destinations respectively (the step can be executed by referring to the address information 54A shown in FIG. 4). Next, the following step can be executed: adjusting the charge strategy information S2 for the destinations corresponding to the time sequences respectively according to the destination data with the time sequences with a view to obtain a task scheduling satisfying the requirements of these destinations. Then, the following step can be further executed: re-calculating the destination data with the time sequences by the processor 120 after the work at each of the destinations is finished in order to make sure that each of medical devices 60 always has enough battery level when the healthcare worker visits each of the destination.

To sum up, according to the portable medical device and the management method thereof disclosed by the embodiments of the disclosure, the processor can calculate the power supply arrangement, implemented during the time period of the healthcare worker moving from the hospital or clinic to the next destination, for the medical devices based on the device management information and the preloaded checklist transmitted through the connectors. The charge order and the charge strategy of the medical devices can be determined according to different output voltages, output currents, charging speeds of the medical devices. As a result, the portable medical device can effectively solve the problem of charging discretion under the same charge pattern, and further solve the problem that the charging speeds of some medical devices are insufficient because these medical devices are frequently used. Thus, the portable medical device can make sure that each of the medical devices always has enough battery level when the healthcare worker visits each of the destinations.

Further, the connectors can be connected to the medical devices inside the portable medical bag to obtain the information of these medical devices, such that the above information can be verified and compared with the checklist. Thus, the healthcare worker can take inventory for the medical devices and check the records, including at least the power status, data connection and light indication, of the medical devices inside the portable medical bag. In addition, the inventory information can be also displayed. Thereupon, the convenience of the healthcare worker taking inventory for the medical devices before or after the medical visiting can be further enhanced.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A portable medical device, comprising:
a portable medical bag, configured to contain a plurality of medical devices;
a plurality of connectors, respectively connected to the plurality of medical devices and the portable medical bag, wherein the portable medical bag is configured to obtain a device management information, having a remaining power, of each of the plurality of medical devices via a corresponding one of the plurality of the connectors; and
a processor, disposed in the portable medical bag and configured to receive a medical device information, a positioning information and an address information, wherein the medical device information includes a battery capacity and a charging specification of each of the plurality of medical devices, and the processor is configured to calculate a charge strategy information of the plurality of medical devices according to the medical device information, the address information and the device management information;
wherein the processor is configured to receive a medical condition, an inspection requirement, and a device usage information, and calculate the charge strategy information according to the medical device information, the address information, the device management information, the medical condition, the inspection requirement, and the device usage information, the charge strategy information including a power supply arrangement specifying a corresponding charge order and charge strategy for each of the plurality of medical devices.

2. The portable medical device of claim 1, wherein the processor is configured to output an inventory information via the medical device information and the device management information, and the inventory information includes a power status, a connection status and a light indication of each of the plurality of medical devices.

3. The portable medical device of claim 2, further comprising a display unit disposed in the portable medical bag and configured to display the inventory information.

4. The portable medical device of claim 1, wherein the address information comprises destination data with time sequences corresponding to a plurality of destinations respectively, and the processor is configured to adjust the charge strategy information for the destinations corresponding to the time sequences respectively according to the destination data with the time sequences.

5. The portable medical device of claim 4, wherein, after work at each of the destinations is finished, the processor is configured to adjust the destination data with the time sequences and obtain a task scheduling conforming to the requirements of the destination data.

6. A management method of portable medical devices, comprising:
receiving a medical device information, a positioning information and an address information by a processor, wherein the medical device information comprises a battery capacity and a charging specification corresponding to a plurality of medical devices;
connecting a plurality of connectors to a portable medical bag and the plurality of medical devices respectively;
obtaining a device management information from each of the plurality of medical devices via the connectors and transmitting the device management information to the portable medical bag, wherein the device management information comprises a remaining power;
receiving a medical condition. an inspection requirement. and a device usage information by the processor; and
calculating a charge strategy information of the plurality of medical devices by the processor according to the medical device information, the address information and the device management information, the medical condition, the inspection requirement, and the device usage information, the charge strategy information including a power supply arrangement specifying a corresponding charge order and charge strategy for each of the plurality of medical devices.

7. The management method of portable medical devices of claim 6, further comprising:
outputting an invention information according to the medical device information and the device management information by the processor, wherein the invention information comprises a power status, a connection status and a light indication of each of the plurality of medical devices.

8. The management method of portable medical devices of claim 7, further comprising:
   displaying the inventory information by a display unit.

9. The management method of portable medical devices of claim 6, further comprising:
   receiving destination data with time sequences by the processor corresponding to a plurality of destinations respectively; and
   adjusting the charge strategy information for the destinations corresponding to the time sequences respectively according to the destination data with the time sequences.

10. The management method of portable medical devices of claim 9, further comprising:
    adjusting the destination data with the time sequences by the processor after work at each of the destinations is finished to obtain a task scheduling satisfying the requirements of the destination data.

* * * * *